United States Patent [19]

Taketo

[11] Patent Number: 4,959,313
[45] Date of Patent: Sep. 25, 1990

[54] CELLULAR ENHANCER FOR EXPRESSING GENES IN UNDIFFERENTIATED STEM CELLS

[75] Inventor: Makoto Taketo, Bar Harbor, Me.

[73] Assignee: The Jackson Laboratory, Bar Harbor, Me.

[21] Appl. No.: 64,665

[22] Filed: Jun. 22, 1987

[51] Int. Cl.$^5$ .................... C12N 15/00; C12P 21/00; C07H 15/12

[52] U.S. Cl. .................... 435/69.1; 435/70.1; 435/172.1; 435/172.3; 435/320; 935/6; 935/33; 935/36; 935/34; 536/27

[58] Field of Search ............... 435/68, 91, 170, 172.1, 435/172.3, 240.2, 320, 252.3, 252.33; 935/6, 9, 26, 27, 29, 31, 32, 36, 57, 70, 73

[56] References Cited

U.S. PATENT DOCUMENTS 4,663,281  5/1987  Gillies et al. .................... 435/68

OTHER PUBLICATIONS

Linney et al (1983), Cell 35:693–699.
Sorge et al (1984), PNAS 81:6627–6631.
Taketo, M. et al, "Isolation of Embryonal Carcinoma Cell Lines That Express Integrated Recombinant Genes in Undifferentiated Embryonic Stem Cells", *Proc. Natl. Acad. Sci. USA*, vol. 82, pp. 2422–2426 (1985).
Taketo, M. et al., "A Cellular Enhancer of Retrovirus Gene Expression in Embryonal Carcinoma Cells," *Proc. Natl. Acad. Sci. USA*, vol. 84 (1987).

Primary Examiner—Richard A. Schwartz
Assistant Examiner—Anne Brown
Attorney, Agent, or Firm—Daniel H. Kane

[57] ABSTRACT

A novel cellular enhancer nucleotide sequence causes expression in undifferentiated stem cells of a flanking exogenous or recombinant gene from a promoter accompanying the gene where the gene and promoter are not normally expressed in the undifferentiated stem cells. In the preferred example the essential or basic core of the cellular enhancer nucleotide sequence is CCTGGGCTCTACAGCAGAAGTCTAAGGGGAAAAGCT
TAGGGAGGAATGCCTGGCAAAGGCCCTCATTACTTA
AGAAACAAGTCCTGACTTCAAAGTGAGCTCCCC.

The cellular enhancer may encompass a more general core sequence of approximately, for example, in the range of 300 to 350 bases including the essential or basic core sequence. Recombinant vectors including plasmids and viruses are constructed bearing the novel cellular enhancer flanking a recombinant or exogenous gene and promoter having a specified phenotypic trait to be expressed in undifferentiated stem cells. Propagating cells containing the vector constructs reproduce and propagate the vectors. Undifferentiated stem cells including cell lines and animals express the desired phenotypic trait of an exogenous or recombinant gene under the control of the novel cellular enhancer.

22 Claims, 4 Drawing Sheets

```
   1 GCTGCAGGTCGAGGGATCCAGCAACACCTGGGCCCAAGACAAGCAAGCGG

51 GAGTCACTAAAGCCCACTTCTAGGTGTTTACAGACTAGAGCAGGAGGTGG
                                                    ─────
                                                      a
 101 AAATGCCCAATGCTGCCTGTAGCCCACAGTCCTTGCATTTCCCTGGATTT
     ────                                         ───────
                                                     b
 151 GGGTCCTCAGGAACCGGAAGTAGGGCCTGCTTGCCCCCACACCACCGCTT

201 TCTTCCCCAAACCACCAGATCTTTCTGGTAGCCAGGCACATATTTCCCGA
             ─────────
                 c
 251 AGAATGAAGTCTAGAGTGGGACAGGAGACCCTTGCCTCCCCCTGCCACCT

301 CGCCCACAAAGACATACACACACACACACACACACACACACACAGTAGCA
                     ──────────────────────────────
                                    d
 351 GTAGTCAAAACAAAGGGTTCCTTATAAGAGTGCCTCATCTATACTTACAG

401 AATTCATGTCAGACCCAACACCTAGCCCTATGCTTGGCCAGTGTACATAG

451 AGGGTTGTGTGTGTGTGTGTGTGTGTGTGTGTGTGTGTGTGTGTGTGTGT
        ──────────────────────────────────────────────
         e
 501 GTGTGTGTGTGTGTTGTGTCTCCAATGGCTGCTTTCCGGAACCCCCAAAG
     ─────────────────────────────────────────────────
 551 CAGCATAAATTGAGTTTAGGATGGACACAGAAATTTGGAAAGAGGAAGCA
     ─────────────────────────────────────────────────
                                   f       215◄─┐
 601 ACTAATCAACAATGAACTAGAGATGGGACCTTGTCCACAGAGCATTGCCT
     ─────────────────────────────────────────────────
 651 GGGCTCTACAGCAGAAGTCTAAGGGGAAAAGCTTAGGGAGGAATGCCTGG
     ──────────────────────────────────────────────────
      └─►d6                              └─►d7    g
 701 CAAAGGCCCTCATTACTTAAGAAACAAGTCCTGACTTCAAAGTGAGCTCC
     ──────────────────────────────────────────────────
     214◄─┐                                  └─►d8
 751 CCAGTCCTTAGTATCCCTCACCTGAAGTCCTGAGGCTCTGTTTCCCTACT
     ─────────────────────────────────────────────────
                          213◄─┐ 200◄─┐
 801 GGGGTCCACACTTGTTAACTGCCTAAGCTCAGATCAGCAGCTGCATATCC
     ─────────────────────────────────────────────────
 851 TGTTTCTTCCCTGAATTTAGGCTCAAACTAATTCACTGCTTTGTTTTGTT
     ─────────────────────────────────────────────────
     └─►d9                                    h
 901 GTTACCTTTTGTTTGAGTTTAAGTTGGGGAGTGGGGGAGTGGGGGGTGG
     ────────────────────────────────────────────────
                           i
 951 GGGTGGGGGGTAGTCTTACTTAGCCCAGAATAGGATGACAAACTGTCTTG
     ──────────

1001 CCTCCACTTCTCAAGTACTAGTGATCCTGAAGTGATGTGTCATTGTCATC

1051 CTGGCAGCTTTTGCTCTTTTTCATTCTTCTTTCTATAACCTTCACCTCCC
                 ─────────────             ─────────────
                       j                         k
1101 CCCCCCATGCCACCCTCAGTTTTGGATGGATTCTAGAAGTGCTGGTGGG
     ─────────────────────────────────────────────────
1151 AAAAATTATTATTTTTCTTAGTTGTTTTAATTGTATTTAACCTTTTCCAT
     ─────────────────────────────────────────────────
       l
1201 CTAAAGTTGTGTAGCATGATGATTTAAAATGTGAAAATAGAGGGTCTTT
     ─────────────────────────────────────────────────
```

"CORE"

"PRIME"

to a method for identifying, isolating, propagating, synthesizing, and utilizing cellular enhancers for expressing recombinant or exogenous genes in undifferentiated stem cells of any species for purposes of, for example, insertion mutagenesis or vector expression production of desired proteins.
CELLULAR ENHANCER FOR EXPRESSING GENES IN UNDIFFERENTIATED STEM CELLS The U.S. Government has rights in this invention by reason of National Institutes of Health grant support, primarily NIH Grant Number CA39652, Makoto Taketo, The Jackson Laboratory, Bar Harbor, Maine 04609, principal investigator, and other related grants.

TECHNICAL FIELD

This invention relates to a new cellular enhancer nucleotide sequence for expressing recombinant or exogenous genes in undifferentiated stem cells; to vector constructs bearing the novel cellular enhancer flanking exogenous or recombinant genes having phenotypic traits to be expressed: to cell lines propagating the vector constructs: and to undifferentiated stem cell lines and animals expressing desired phenotypic traits of exogenous origin. More generally the invention relates to a method for identifying, isolating, propagating, synthesizing, and utilizing cellular enhancers for expressing recombinant or exogenous genes in undifferentiated stem cells of any species for purposes of, for example, insertion mutagenesis or vector expression production of desired proteins.

BACKGROUND ART

Murine embryonal carcinoma (EC) cells, undifferentiated stem cells of teratocarcinoma, share many features with embryonic stem cells. See, for example, Strickland, S., 1981, Cell Vol. 24: 277-278. One such property is that they are refractory to infection by viruses such as retroviruses and papovaviruses as shown by Teich, N.M., Weiss, R.A., Martin, G.R. & Lowy, D.R. (1977) Cell Vol. 12: 973-982; Swartzendruber, D.E. & Lehman, J.M. (1975) J. Cell. Physiol. Vol. 85: 179-188. This regulation appears to be primarily at the level of transcription, see Gorman, C.M., Rigby, P.W.J. & Lane, D.P. (1985) Cell Vol. 42: 519-526, although posttranscriptional blocks have also been proposed by Segal, S. & Khoury, G. (1978) Proc. Natl. Acad. Sci. U.S.A. Vol. 76: 5611-5615.

Polyomavirus host-range mutants that can propagate in EC cells have been found to contain point mutations and/or rearrangements in the viral enhancer region, suggesting that the wild-type viral enhancer does not normally function in EC cells. For a review, see Amati, P. (1985) Cell Vol. 43: 561-562. Further, it has been proposed by Linney, E., Davis, B., Overhauser, J. & Fan, H. (1985) Nature (London) Vol. 308: 470-472, that the Moloney murine leukemia virus (Mo-MuLV) regulatory sequence acting as an enhancer element in differentiated cells does not function in EC cells.

A previous report by the present inventor, Taketo, M., with collaborators Gilboa, E. & Sherman, M.I. (1985) Proc. Natl. Acad. Sci. U.S.A. Vol. 82: 2422-2426, describes the isolation of clonal transductant EC cell lines that express the neomycin-resistance gene neo linked to the Mo-MuLV long terminal repeat (LTR). The integrated recombinant viral gene is stably expressed despite the fact that these EC cells remain undifferentiated. The lack of helper provirus expression and the results of superinfection studies set forth in this reference suggest that the expression of the neo gene in the EC lines is due to cis-acting mechanisms. It is a discovery of the present invention that in at least one such transductant EC cell line, the LTR-linked neo gene is expressed because the provirus was integrated in the vicinity of a cellular enhancer. This cellular enhancer is active in EC cells and causes the neo gene to be transcribed from the bona fide LTR promoter. On the other hand, the natural enhancer of the LTR has little activity in EC cells.

A recent paper by Barklis, E., Mulligan, R.C., and Jaenisch, R. (1986) Cell Vol. 47: 391-399 characterizes recombinant proviruses expressed in F9 cells. Expression of some of the proviruses was mediated by the 5' flanking cellular sequences. It is possible that these flanking sequences contain cellular enhancer elements, unrecognized, unknown or unreported by the authors, similar to the novel cellular enhancer of the present invention. The present inventor has no further knowledge of this work and believes he is the first to identify, isolate, sequence, and propagate a novel and potentially powerful cellular enhancer operative in undifferentiated embryonic stem cells for transcription and expression of exogenous recombinant genes.

OBJECTS OF THE INVENTION

It is therefore an object of the present invention to provide a new cellular enhancer which causes transcription in undifferentiated stem cells of a substantially flanking exogenous or recombinant gene from a promoter accompanying the gene where the gene and promoter are not normally expressed in undifferentiated stem cells.

Another object of the invention is to provide recombinant vector constructs such as recombinant plasmid vectors or recombinant transducing viral vectors bearing the novel cellular enhancer and an exogenous or recombinant gene having a specified phenotypic trait to be expressed. A feature and advantage of the cellular enhancer is that it is capable of causing transcription and expression of the exogenous gene and phenotypic trait in undifferentiated stem cells transformed, transfected or transduced by the vector construct. For example, according to the invention, a provirus bearing the novel cellular enhancer and an exogenous or recombinant gene having a specified phenotypic trait may be inserted in the genome of an undifferentiated stem cell for transcription and expression of the gene in clones of the undifferentiated stem cells and in animals comprising the transformed, transfected, or transduced cells.

A further object of the invention is to provide cell lines propagating the vector constructs and to provide undifferentiated embryonal stem cell lines and animals expressing the exogenous or recombinant genes with specified phenotypic traits.

More generally, the object of the invention is to provide a method for identifying, isolating, propagating, synthesizing and utilizing cellular enhancers for expressing recombinant or exogenous genes with desired phenotypic traits in undifferentiatd stem cells for any species. The method is intended for expressing recombinant or exogenous genes in undifferentiated stem host cells in which the gene would not normally be expressed.

DISCLOSURE OF THE INVENTION

In order to accomplish these results the present invention provides a novel cellular enhancer nucleotide sequence in either DNA or RNA form which causes expression in undifferentiated stem cells of a flanking exogenous or recombinant gene from a promoter accompanying the gene where the gene and promoter are not normally expressed in undifferentiated stem cells. The invention further encompasses similar sequences derived from, or isolated by cross-hybridization with the novel nucleotide sequence, and to single and multiple mutations, base substitutions, insertions, deletions, duplications, inversions and transpositions or other genetic rearrangements of the basic sequence, which also cause expression in undifferentiated stem cells of the flanking exogenous or recombinant gene.

According to the preferred example embodiment of the invention, the essential or basic core of the cellular enhancer nucleotide sequence comprises

CCTGGGCTCTACAGCAGAAGTCTAAGGGGAAAAGCTTAGGGAGGAATGCCTGGCAAAGG-

CCCTCATTACTTAAGAAACAAGTCCTGACTTCAAAGTGAGCTCCCC.

While the essential or basic core sequence comprises approximately 105 bases or slightly greater than 100 bases, the cellular enhancer may encompass a more general core sequence of approximately, for example, in the range of 300 to 350 bases including the essential or basic core sequence of approximately 105 or slightly greater than 100 nucleotide bases. See Taketo, M., and Tanaka, M. *Proc. Natl. Acad. Sci. U.S.A.* Vol. 84: 3748-3752 (1987).

Among the identifying features of the general core sequence is an enhancer core consensus sequence TGGAAAG upstream with reference to the direction of transcription of the proviral genome originally flanking the enhancer. See Taketo, M. and Tanaka, M. Proc. Natl. Acad. Sci. U.S.A. Vol. 84: 3748-3752 (1987). The basic core sequence in the range of approximately 105 or slightly greater than 100 bases includes an enhancer core-like sequence TGGCAAAG.

The invention also provides recombinant vector constructs such as plasmids, cosmids, bacteriophages, DNA viruses, RNA viruses and retroviruses, bearing the novel cellular enhancer flanking a recombinant or exogenous gene with a promoter having a specified phenotypic trait to be expressed in undifferentiated stem cells. For example, according to the invention a provirus is integrated in the genome of an undifferentiated embryonic stem cell. The provirus bears an exogenous or recombinant gene with a promoter having a specified phenotypic trait to be expressed in undifferentiated embryonic stem cells flanking the novel cellular enhancer. Expression of the phenotypic trait may be for example for purposes either of expression vector production of a desired protein or for insertion mutagenesis.

In further embodiments the invention provides cells containing the vector constructs for producing or propagating the vectors. Such cells are selected from the group, for example, consisting of *Escherichia coli*, host animal cells, NIH3T3 fibroblasts, mouse embryonic stem cells (ES cells or EK cells), embryonal carcinoma (EC) cells, primordial germ (PG) cells, and early embryo cells. The invention also provides undifferentiated stem cells for cell lines and in animals capable of bearing and expressing the desired phenotypic trait of an exogenous or recombinant gene under the control of the novel cellular enhancer. According to the invention the cellular enhancer can be inserted in the stem cell genome together with the flanking recombinant gene and promoter. The cellular enhancer, exogenous gene and promoter may consitute an assembled or constructed recombinant sequence from a bacterial plasmid vector or a provirus from a transducing retrovirus vector.

According to a preferred example embodiment of the method, the invention contemplates expressing a recombinant proviral gene in undifferentiated embryonic stem cells in which the provirus gene is not normally expressed by assembling or constructing a recombinant DNA sequence comprising an LTR-linked recombinant provirus gene having a specified phenotypical trait to be expressed, a corresponding LTR promoter, and a flanking cellular enhancer derived from undifferentiated embryonic stem cells. The cellular enhancer causes transcription from the LTR promoter of the provirus gene in undifferentiated embryonic stem cells. The method includes transducing the recombinant DNA sequence into other undifferentiated stem host cells for expression of the provirus gene in cell lines and in animals. Other objects, features, and advantages of the invention are apparent in the following specification and accompanying drawings.

BRIEF DESCRIPTION OF THE DRAWINGS

FIG. 1 is a schematic diagram or map of structures and transfection efficiencies of recombinant plasmids derived from lambda (λ) phage clone D. 1.5pmol of each plasmid DNA in supercoiled form were mixed with carrier salmon sperm DNA to make up 20 μg of DNA mixture and added to PCC4.azalR cells as described in *Example Materials and Methods*. Solid bars indicate mouse genomic sequences. Hatched bars indicate Mo-MuLV LTR sequences derived from the lambda (λ) phage clone D. Dotted or stippled bars indicate the neo gene segment. Cross-hatched bars are HSV-tk promoter sequences. Thick open bars indicate Mo-MuLV sequence containing LTR. Thin open bars are sequences derived from SV40 genome. The portions derived from vectors are not shown. White arrows or open arrows indicate the direction of the neo gene transcription. Black arrows or solid arrows indicate the orientations of the 2.3-kb mouse genomic fragment. Abbreviations for the restriction sites are as follows: Bm, BamHI; RV, EcoRV: Cl, Cla I: Xh, Xho 1: Sm, Sma I: Sl, Sal I: Ac, Acc I; Hd, HindIII; Bg, Bgl II. Only relevant restriction sites are shown. Transfection efficiencies are given as number of G418-resistant colonies per dish.

FIG. 2A is an autoradiograph of labelled RNA probe fragments protected from RNase digestion after hybridization with total cellular RNA from transfected EC cells. Transiently expressed RNA was hybridized with excess RNA probes, digested with RNase and electrophoresed on a denaturing polyacrylamide gel. Lanes 1-4 of the gel show RNA preparations hybridized with the HindIII probe of lane 5. Lanes 6-9 show RNA preparations hybridized with the Xba I probe of lane 10. Transiently expressed RNA was prepared from PCC4.azalR cells transfected with the plasmids pDN7 (lanes 1 and 6), pLN4 (lanes 2 and 7) and pUC18 (lanes 3 and 8) or from mock-transfected cells (lanes 4 and 9). Nucleotide lengths of the corresponding RNA fragments are indicated on the left whereas those of the size markers are on the right. FIG. 2B is a schematic diagram of the hybridization mapping experiments. The template plasmid pGL1 for synthesizing the anti-sense RNA probes was constructed by inserting the Xho I-Bgl II segment of pDN7 (FIG. 1) into the vector pGEM1, available from Promega Biotec, Madison, WI, U.S.A., at the multiple cloning site (MCS) The radiolabelled RNA probes were transcribed in vitro from the T7 promoter of pGL1 to the HindIII site (converted from Sma I site) or to the Xba I site using the templates linearized at these sites. Abbreviations for restriction sites are as follows: Xh, Xho I; Sl, Sal I: Xb, Xba I: Ss, Sst I: Hd, HindIII: Sm, Sma I; Bm, BamHI. Only relevant restriction sites are shown.

FIG. 3A is a graph showing the effects of deletions introduced at the downstream end (Xho I site) of the 2.3kb segment in the test plasmids pDN7 and pDN3 of FIG. 1. FIG. 3B is a graph showing the effects of deletions at the upstream end (Cla I site) of the 1.2kb enhancer-containing segment in the plasmid pDN207A and pDN207. Broken lines at the bottom of FIGS. 3A and 3B represent deleted portions whereas solid lines indicate remaining portions of the cellular fragment in the deletion constructs. The upward arrows show the deletion endpoints at which the number of these constructs are placed. Filled circles describe results with the deletion derivatives of pDN7 in FIG. 3A and pDN207A in FIG. 3B that carried the polyadenylylation signal upstream of the enhancer segment. The results with deletion derivatives of pDN3 shown in FIG. 3A and pDN207 shown in FIG. 3B that did not have the upstream polyadenylylation signals, are shown by the open circles in the figures. Transfection efficiencies are presented as percentages relative to the activity with the parental plasmids in each deletion series. The number indicated for each deletion derivative is the average percentage obtained in several independent experiments. Actual numbers of transfectant colonies for the parental plasmids (i.e. the numbers taken as 100%) ranged from 418 to 687.

FIG. 4 is a DNA sequence map or code listing of a cellular DNA sequence containing the cellular enhancer fragment. This portion was derived from the 2.3-kb enhancer-containing fragment retained in the deletion subclone pDN203 of FIG. 3A and then sequenced. Only the top strand in the original orientation in pDL1 from FIG. 1 is shown although both strands were sequenced for the entire region presented. Nucleotides are numbered in the conventional 5' to 3' direction at the beginning of each 50 base-line. The endpoints of the enhancer segment retained in some of the deletion constructs of FIGS. 3, 3A, and 3B are shown by arrows. For example, 200-215 indicate deletion constructs derived from pDN3 or pDN7 and d6-d9 indicate derivatives of pDN207 or pDN207A. The lower case letters indicate characteristic sequence stretches described in the specification. The continuous underlining from bases #520 to 869 indicates the "core" region used for similarity analysis. Boldface region indicates the basic core sequence or segment essential for the enhancer activity.

DESCRIPTION OF PREFERRED EXAMPLE EMBODIMENTS AND BEST MODE OF THE INVENTION

Cloning of a neo-containing provirus with its flanking cellular sequences, and determination of transfection efficiency was achieved according to the invention as follows. To obtain more single-copy-integration transductants than previously reported by the inventor in Taketo, M., with collaborators Gilboa, E. & Sherman, M.I. (1985) Proc. Natl. Acad. Sci. U.S.A. Vol. 82: 2422-2426, EC cell lines PCC4.azalR and F9tk$^-$ were infected at relatively low multiplicities with Fvc-12 transducing virus. This virion-packaged recombinant transducing retrovirus contains the neo gene linked to the LTR of Mo-MuLV and is documented in the foregoing report of Taketo, Gilboa and Sherman (1985) which is incorporated herein by reference. The technique of Southern for blot hybridization analysis of the transductant EC cell DNA was used and showed that most of the clones contained a single proviral insert. This method is described in Southern, E.M. (1975) *J. Mol. Biol.* Vol. 98: 503-517. Five transductant EC cell lines were chosen that yielded neo-containing BamHI or HindIII fragments ranging from 10 to 20 kb. These fragments were cloned into the phage λ vector 2001 documented in Karn, J., Matthes, H.W.D., Gait, M.J., & Brenner, S. (1984) *Gene* 32, 217-224. Since the original Fvc-12 provirus was about 3kb, these fragments provided us with substantial flanking cellular sequences.

To determine whether the genetic signals that allow expression of the LTR-linked neo gene resided in the cloned regions of the transductant EC cell genomes, the parental EC cell lines were transfected with the recombinant λ DNA preparations and scored for G418-resistant EC cell colonies. As shown in Table I, neo-expressing transfectants were obtained in four out of five cases, while the control phage clone R with the LTR-neo sequence alone failed to generate G418-resistant colonies. These results indicate that the cloned segments of some of the transductant EC cell genomes contained the genetic signals leading to expression of the LTR-linked neo gene upon transfection. It was noted that a phage clone derived from transductant EC cell line D showed 30 times higher transfection efficiency with the parental PCC4.azalR cell than with F9tk$^-$ cells, whereas transfectants were obtained with a phage clone derived from the transductant line C only with parental F9tk$^-$ cells. The phage clones derived from transductant EC cell lines B and F produced transfectants from both PCC4.azalR and F9tk$^-$ cells. This is reminiscent of various polyoma host-range mutants that propagate differentially in various EC cell lines as reported by Melin, F., Pinon, H., Reiss, C., Kress, C., Montreau, N. & Blangy, D. (1985) *EMBO J.* Vol. 4: 1799-1803.

The novel cellular enhancer element according to the invention was derived from the transductant EC cell line D as follows. From the λ recombinants of Table I clone D was chosen for further analysis because of its high transfection efficiency. The entire BamHI insert of the phage λ clone D was recloned into the plasmid pUC18, and several subclones covering various parts of the insert were subsequently constructed. Subclones containing the 5' flanking cellular sequence in addition to the LTR-neo sequence were efficient in transfection assays with PCC4.azalR EC cells, suggesting an enhancer-like activity in the upstream flanking sequence (data not shown).

Figure 1:
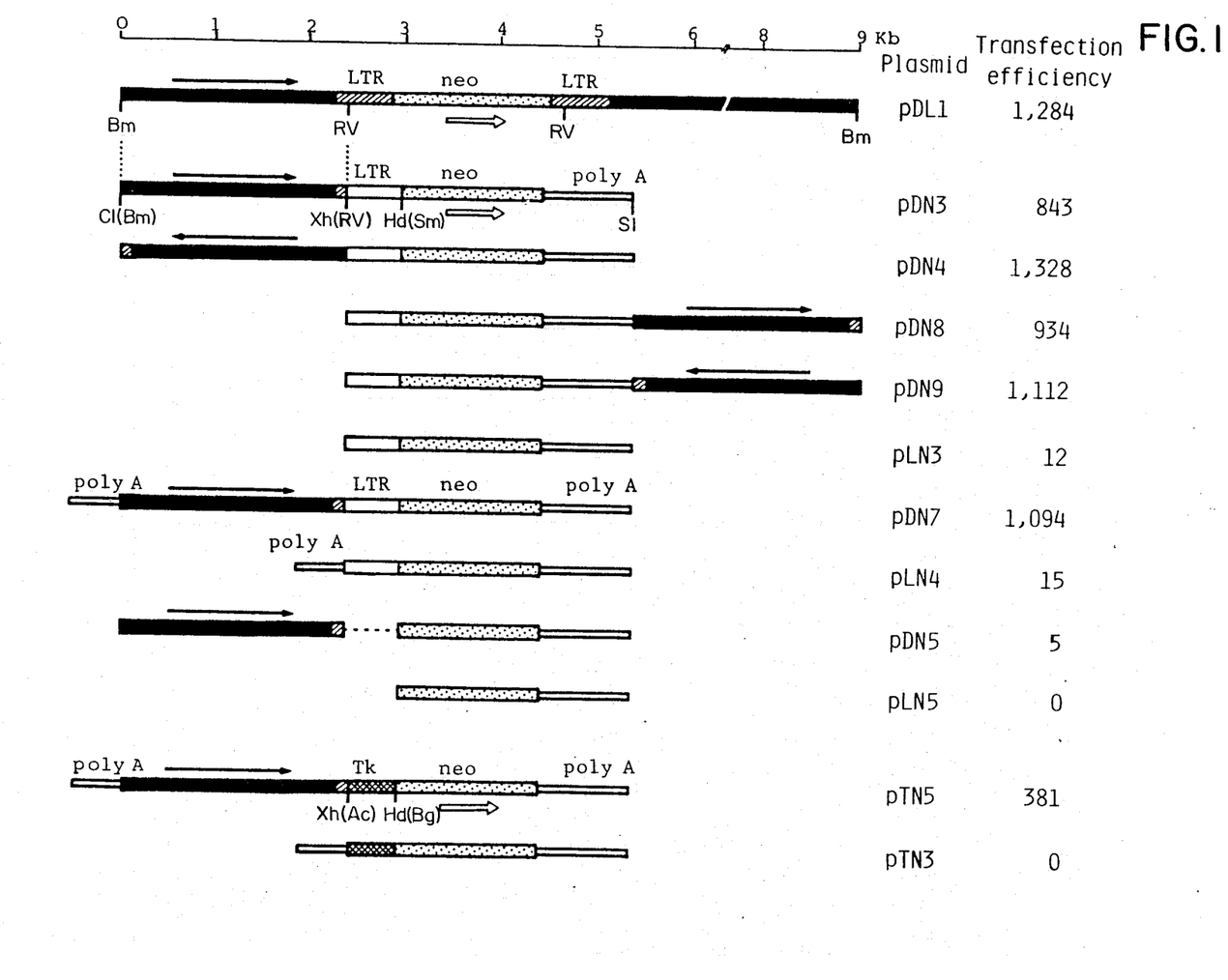

The 2.3-kb 5' flanking cellular sequence was then subcloned into the plasmid pLN3 containing the LTR-neo sequence, at either an upstream or a downstream position and in both orientations as shown in FIG. 1. When these test constructs were assayed by transfection, the 2.3-kb fragment increased the efficiency 70- to 110-fold over the basal level obtained by the LTR-neo sequence alone in pLN3. The stimulation of the transfection efficiency was similar whether the 2.3-kb fragment was inserted at the position upstream (pDN3 and pDN4) or downstream (pDN8 and pDN9) of the LTR-neo sequence, and the enhancing effect of the 2.3-kb fragment was observed in both orientations all as summarized in FIG. 1.

To examine the possibility of read-through transcription from upstream promoters in the vector sequence, we tested the effect of the polyadenylylation signal inserted upstream of the test sequences. This segment, derived from the SV40 early region, had no significant effect on the transfection efficiency with either the LTR-neo control construct (pLN4 vs. pLN3) or the construct with the 2.3-kb fragment (pDN7 vs. pDN3). Removal of the LTR sequence reduced the transfection efficiency dramatically in both constructs with and constructs without the 2.3-kb fragment (pDN5 vs. pDN3, and pLN5 vs. pLN3, respectively). All data are summarized in FIG. 1.

Addition of the 2.3-kb fragment upstream of the HSV tk promoter linked to the neo sequence (pTN5) caused efficient expression of the neo gene, whereas the test sequence alone without the 2.3-kb fragment (pTN3) did not generate any stable EC cell colonies. These data are also summarized in FIG. 1.

Figure 2A:
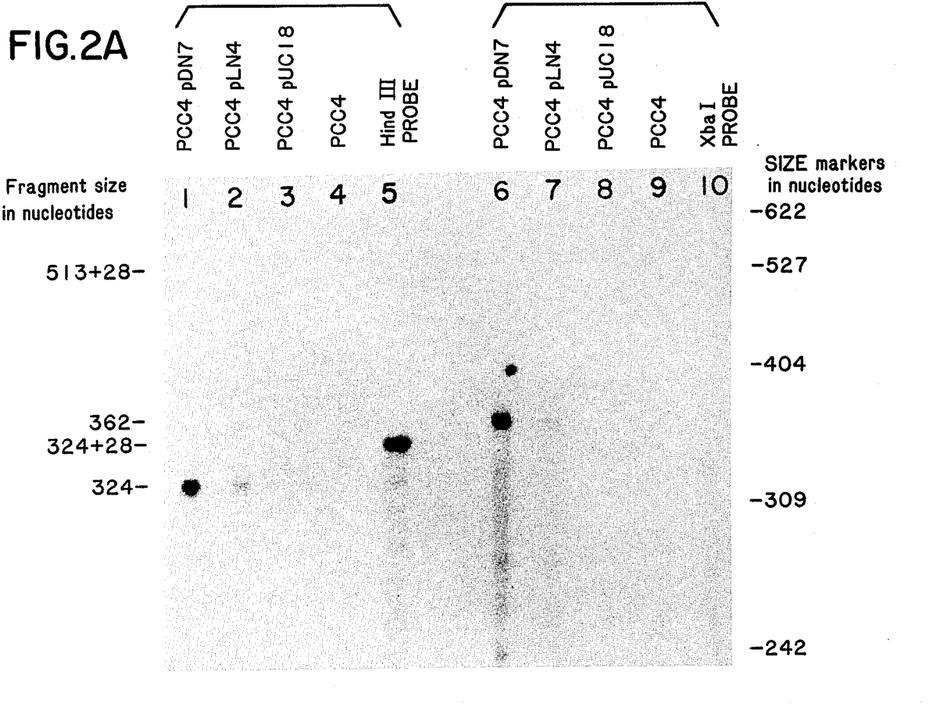
FIGS. 2A and 2B show the hybridization mapping of the 5' end of transiently expressed neo gene transcripts.
Figure 2B:
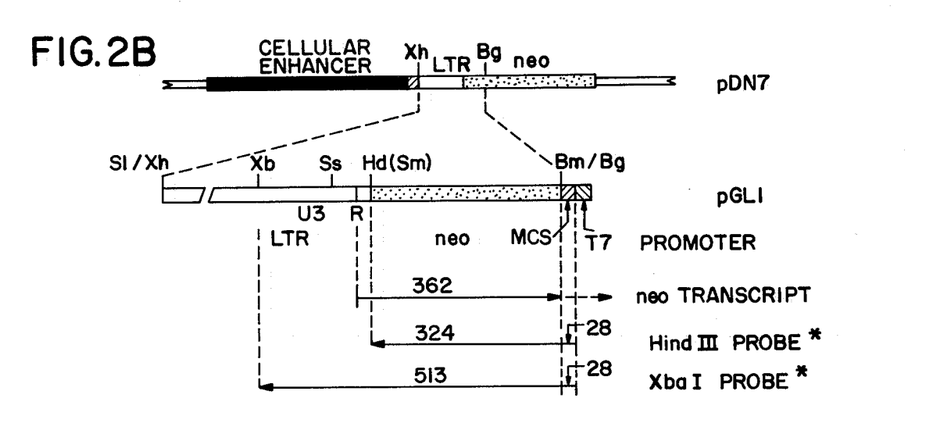

Mapping of the 5' end of the neo gene transcripts was accomplished as follows. Transiently expressed neo gene transcripts in EC cells transfected by the test plasmids with or without the 2.3-kb cellular enhancer fragment were analyzed. For these analyses, RNA hybridization probes transcribed in vitro from a template plasmid carrying the LTR-neo sequence linked to the T7 phage promoter were used as shown in FIGS. 2A and 2B. By digesting this template plasmid at the HindIII and Xba I sites, respectively, two kinds of labeled antisense RNA probes (run-off transcripts) were prepared. The probes had 324- and 513-nucleotide hybridizable sequences, respectively, in addition to the 28 extra nucleotides derived from the multiple cloning site of the vector as shown in lanes 5 and 10, respectively of FIG. 2A. Total cellular RNA from PCC4.azalR cells transfected with the enhancer-containing plasmid pDN7 was hybridized with the HindIII probe. The resulting protected fragment was about 324 bases long as shown in lane 1 of FIG. 2. This was shorter than the probe only by the length corresponding to the multiple cloning site. The RNA from the cells transfected with the test construct without the cellular enhancer fragment (pLN4) also possessed a protected fragment of the same length as that of pDN7 as shown in lane 2. Hybridization with the Xba I probe protected a fragment of about 362 bases in RNA preparations from both pDN7- and pLN4-transfected EC cells shown in lanes 6 and 7, respectively, indicating that the transcription was initiated about 40 bases upstream of the HindIII site. Transcription was thus initiated at the junction between the U3 and R regions of the LTR, the bona fide cap site, illustrated in the schematic diagram of the hybridization map of FIG. 2B. With both probes there was about 10 times more hybridizable transcript in the pDN7-transfected cells than in the pLN4-transfected cells as determined by densitometry of the autoradiographs.

The neo transcript stably expressed in the transductant EC cell line D was also mapped as well as the neo transcripts transiently expressed after transfection of PCC4.azalR cells with the plasmid pDL1. The results indicated that the transcription was initiated at the bona fide transcription initiation site in the LTR as defined in differentiated cells, and the same site as mapped in the transiently expressed test plasmids presented above (data not shown). These results indicate that the 2.3-kb cellular DNA fragment contains an element meeting the criteria for a classical enhancer as established by Khoury, G. & Gruss, P. (1983) *Cell* Vol. 33: 313–314.

Figure 3:
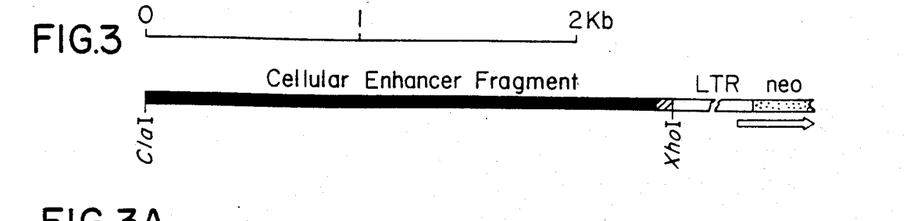
FIGS. 3, 3A and 3B are diagrammatic graphs showing deletion analysis of the enhancer-containing fragments. The basic cellular enhancer fragment is shown in the diagrammatic graph or map of FIG. 3.
Figure 3A:
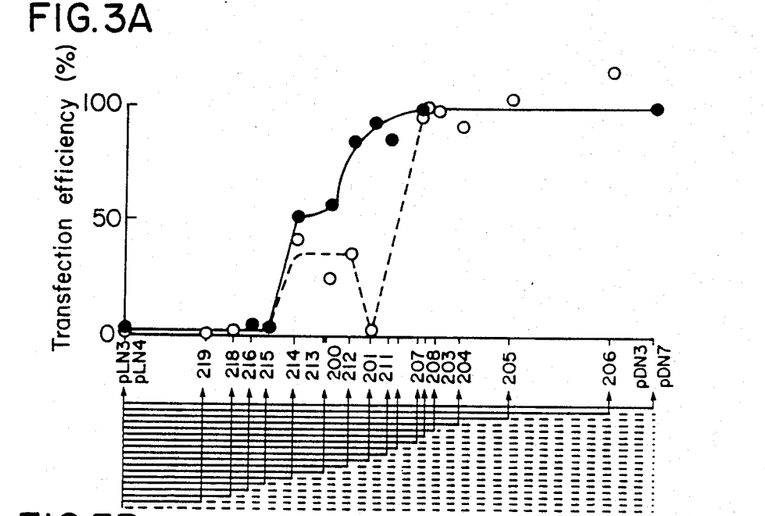

Deletion analysis of the enhancer-containing fragment of FIG. 3 was carried out as follows. FIG. 3A shows the effect of deletions introduced with BAL-31 nuclease at the downstream end of the 2.3-kb cellular fragment (Xho I site in plasmids pDN7 and pDN: see FIG. 1 and *Example Materials and Methods*). When assayed with the deletion constructs carrying polyadenylylation signals at the upstream end of the enhancer fragment (derivatives of pDN7), deletions longer than that in the plasmid pDN207A caused gradual loss of the transfection efficiency to about 50%, until the deletion reached its position in pDN214A. Beyond the latter deletion endpoint, the activity decreased sharply and was completely abolished beyond the deletion endpoint of pDN215A. With deletion constructs lacking polyadenylylation signals (derivatives of pDN3), the enhancer activity was lost transiently in the deletion plasmid pDN201, was partially recovered in longer deletions, and was eventually lost once again beyond the deletion endpoint in pDN215.

Figure 3B:
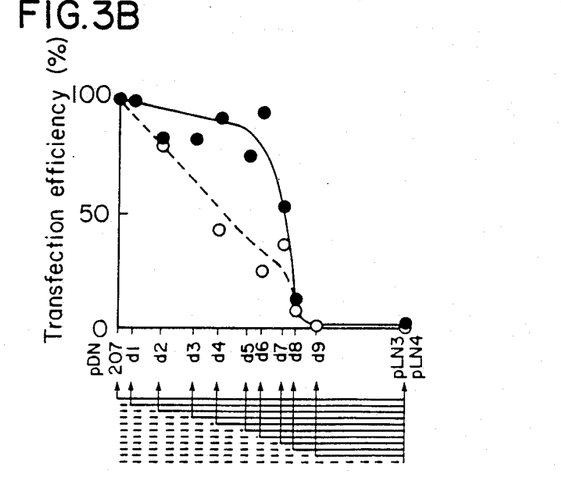

We constructed another series of deletions beginning at the upstream end (Cla I site) of pDN207A and pDN207. As shown in FIG. 3B, the enhancer activity decreased sharply in deletions beyond that of the plasmid pDN207d6A in derivatives of pDN207A that carried the polyadenylylation signal. When the deletion constructs lacked polyadenylylation signals (derivatives of pDN207), the transfection efficiency decreased gradually, starting at the very upstream end of the 1.2-kb cellular fragment.

These results demonstrated two segments that were essential for the enhancer activity: namely, the segment between the deletion endpoints of pDN214A and pDN215A, FIG. 3A, and the segment between pDN207d6A and pDN207d8A, FIG. 3B. These segments overlapped almost entirely, as confirmed by DNA sequence analysis described below. The segment between deletion endpoints of pDN207A and pDN200A doubled the overall enhancer activity, although it was not essential.

Figure 4:
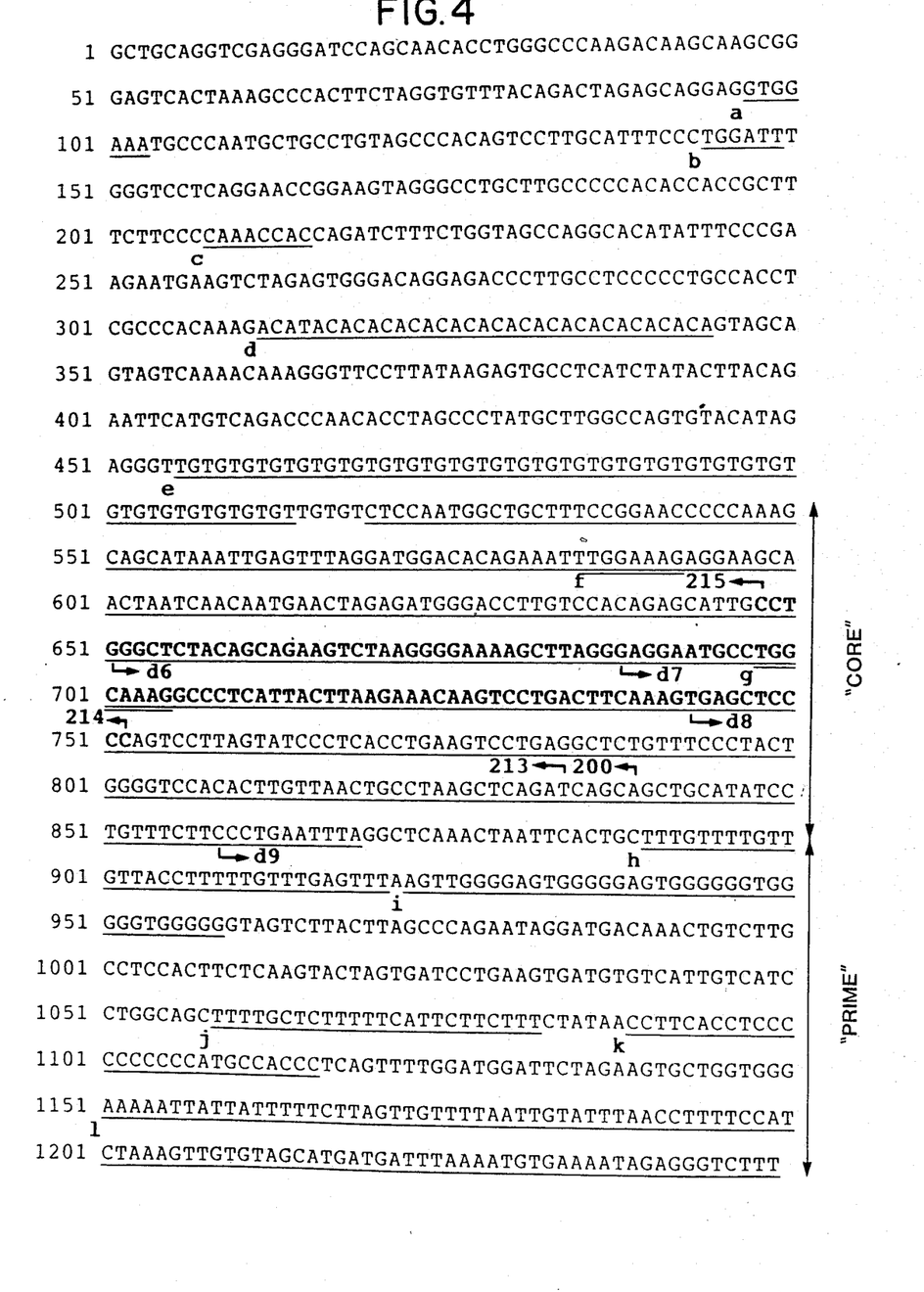

Determination and analyses of the novel cellular enhancer DNA sequence were as follows. As shown in FIG. 4, the DNA sequence of the region of the 2.3-kb enhancer-containing fragment covered by the deletion construct pDN203 of FIG. 3A was determined. At the same time the sequences of deletion endpoints of some of the deletion constructs described in FIG. 3 were determined. The two essential segments described above overlap almost entirely and span about 100 bases as shown in boldface in FIG. 4.

The sequence contained the following distinct characteristics: (i) enhancer-core consensus sequences reported by Weiher, H., Konig, M. & Gruss, P. (1983) *Science* 219, 626–631, GTGGAAA (underline a in FIG.

4), TGGATT (underline b), CAAACCAC (underline c), and TGGAAAG (underline f), and an enhancer core-like sequence, TGGCAAAG (underline g): (ii) two long stretches of purine/pyrimidine alternating sequences (underlines d and e) that could form a Z-DNA structure as described in Rich, A., Nordheim, A. & Wang, A. H.-J. (1984) *Annu. Rev. Biochem.* 53, 791-846: (iii) a T-rich stretch (underline h): (iv) five G-rich tandem repeats (underline i): (v) another T-rich stretch (underline j); (vi) a C-rich stretch (underline k): and (vii) an A+T-rich stretch (underline l), all as shown in FIG. 4. Sequences (i) and (ii) were not essential for enhancer activity because their deletion did not affect the activity as shown by the data for pDN207d6A in FIG. 3B.

The GenBank DNA sequence files of the National Institutes of Health, Genetic Sequence Databank, GenBank (Research Systems Div., Bolt, Beranek, and Newman, Cambridge, MA) Tape Release 40.0, was screened for documented sequences identical or similar to this cellular sequence. For this purpose the upstream region containing the purine/pyrimidine alternating segments was eliminated and the rest of the sequence was divided into two parts: the "core" region, bases 520-869 with continuous underlining in FIG. 4, and the "prime" region, bases 870-1249, flanking the downstream end of the core region. The core region contains the basic core of the cellular enhancer segment essential for the enhancer activity, whereas the prime region contained several subregions of various characteristic stretches rich in particular bases.

Computer-assisted statistical screening of the GenBank files against both the core and the prime regions identified no statistically significant similarity. A search for local similarities of the cellular enhancer sequence with published enhancer sequences was also conducted. The results demonstrated that the core region of this cellular enhancer contained many subregions that were similar to various viral and cellular enhancer elements. However, the extent of similarity in the best match alignments ranged from no greater than 55% to 70% (data not shown).

TABLE I

Transfection of EC cells with cloned DNA segments carrying a neo-containing proviral genome and flanking cellular sequences isolated from G418-resistant transductant EC cell lines.

| Transductant EC Cell Line | Parental EC Cell Line | λ Phage Clone | No. of Resistant Colonies F9tk⁻ | No. of Resistant Colonies PCC4.azaIR |
|---|---|---|---|---|
| A | F9tk⁻ | λA | 0 | 0 |
| B | F9tk⁻ | λB | 17 | 48 |
| C | F9tk⁻ | λC | 15 | 0 |
| D | PCC4.azaIR | λD | 3 | 85 |
| F | PCC4.azaIR | λF | 3 | 1 |
|   |   | λR(LTR-neo) | 0 | 0 |

Twenty micrograms (about 0.6 pmol) of each λ clone DNA were transfected into each EC cell line. The indicated colony numbers are averages of two independent experiments. λ R (LTR-neo), which contained the neo gene linked to the Mo-MuLV LTR, was constructed by inserting the HindIII-linearized plasmid pRK4 from Taketo, Gilboa, and Sherman (1985) into λ 2001 at the HindIII site.

EXAMPLE MATERIALS AND METHODS

For transfection of DNA onto EC cells, the procedure of Linney and Donerly described in Linney, E. & Donerly, S. (1983) *Cell* 35, 693-699, was used. After 12 h, G418 was added at 300 μg (titer)/ml and resistant colonies were scored 10 to 12 days later.

Construction of test plasmids was accomplished according to the standard procedures, described in Maniatis, T., Fritsch, E.F. & Sambrook, J. (1982) *Molecular Cloning: A Laboratory Manual* (Cold Spring Harbor Laboratory, Cold Spring Harbor, NY), pp. 382-384, unless otherwise noted. The test plasmids were prepared as follows:

pDL1: The BamHI insert was excised from the λ phage clone D and reinserted into the BamHI site of the plasmid pUC18.

pLN3: The SV40 promoter region (the Acc I-HindIII fragment) of the plasmid pSV2neo documented in Southern, E.M. & Berg, P.J. (1982) *Mol. Appl. Genet.* 1, 327-341, was replaced by the 547-base pair (bp) Pvu II-Sma I fragment of the Mo-MuLV LTR (base numbers 7745-8292 reported in Shinnick, T.M., Lerner, R.A. & Sutcliffe, J.G. (1981) *Nature (London)* 293, 543-548, using HindIII and Xho I linkers.

pDN3: The 2.3 kilobase (kb) BamHI-EcoRV fragment containing the 5' flanking cellular sequence, was excised from pDL1 and inserted into pLN3 at the Xho I site.

pDN4: Preparation of this plasmid was the same as pDN3 except that the 2.3-kb cellular DNA segment was inserted in the opposite orientation.

pDN8: The 2.3-kb BamHI-EcoRV fragment was inserted into the Sal I site of pLN3 using Xho I linkers.

pDN9: Preparation or construction of this plasmid was the same as for pDN8 except that the 2.3-kb segment was in the opposite orientation.

pLN4: This plasmid contained, upstream of the LTR, tandemly duplicated polyadenylylation signals derived from SV40 as described in Kadesh, T. & Berg, P. (1986) *Mol. Cell. Biol.* 6, 2593-2601. The orientation of these additional polyadenylylation signals was the same as those derived from pSV2neo.

pDN7: Tandemly duplicated polyadenylylation signals were introduced into the plasmid pDN3 by replacing the Sal I-Cla I vector fragment with the BamHI fragment from pSV2Agpt that contained the vector and polyadenylylation signals as documented by Kadesh, T. & Berg, P. (1986) *Mol. Cell. Biol.* 6, 2593-2601, using Sal I and Cla I linkers.

pLN5: The Xho I-HindIII LTR segment was deleted from pLN3 and resealed using Xho I linkers.

pDN5: The 2.3-kb BamHI-EcoRV fragment was inserted into the Xho I site of the plasmid pLN5 by means of Xho I linkers.

pTN3: The Acc I-HindIII SV40 promoter fragment of pSV2neo was replaced by the use of HindIII linkers with the HSV thymidine kinase gene (tk) promoter fragment excised from the plasmid pTKcat described by Gorman, C.M., Moffat, L.E. & Howard, B.H. (1982) *Mol. Cell. Biol.* 2, 1044-1051, with Acc I and Bgl II enzymes. Additional polyadenylylation signals were then introduced upstream of the tk promoter by replacing the Acc I-Nde I fragment with the BamHI-Nde I fragment of pSV2Agpt using Xho I linkers.

pTN5: The 2.3-kb BamHI-EcoRV flanking cellular segment was inserted into the Xho I site of the plasmid pTN3.

RNA Analyses were as follows. Total cellular RNA was extracted as described by Payvar, F. & Schimke, R.T. (1979) *Eur. J. Biochem.* 101, 271-282. For analysis of transiently expressed RNA, 1.5 pmol of plasmid DNA (supercoiled form) mixed with carrier pUC18 DNA was transfected onto PCC4.azalR cells seeded two days prior to transfection at a density of 3×10⁵ cells/90 mm dish. After 24 hours, cells were washed and incubated 24 hours further before extraction of RNA. Quantitative mapping of the 5' end of the transcripts was performed according to the method of Melton, D.A., Krieg, P.A., Rebagliati, M.R., Maniatis, T., Zinn, K. & Green, M.R. (1984) *Nucleic Acids Res.* 12, 7035–7056.

Deletion Plasmids were prepared as follows. To introduce deletions at the downstream end of pDN7 and pDN3, supercoiled plasmid DNA was linearized by Xho I, digested with BAL-31 exonuclease, treated with the Klenow fragment of *E. coli* DNA polymerase I, added with Xho I linkers, digested with Xho I and Cla I and inserted into the vector containing fragments by double digestion of pDN7 and pDN3, respectively. To introduce deletions at the upstream ends in the 1.2-kb fragment of pDN207A and pDN207, Cla I linkers were used instead of Xho I linkers.

For DNA sequence analyses, the dideoxynucleotide method was employed using single strand DNA templates as reported in Messing, J. (1983) *Methods Enzymol.* 101, 20–78, or double stranded DNA templates as described in Korneluk, R.G., Quan, F., and Grand, R.A. (1985) *Gene* 40, 317–323. Sequence data obtained in this way were analyzed and manipulated using the computer programs of Smith, T.F., Gruskin, K., Tolman, S. & Faulkner, D. (1986) *Nucleic Acids Res. Vol.* 14: 25–29, and Smith, T.F. & Waterman, M.S. (1981) *J. Mol. Biol.* 147, 195–197 at the Molecular Biology Computer Research Resource (MBCRR), Dana-Farber Cancer Institute, Boston, MA 02115.

While the invention has been described with reference to particular example embodiments, more generally it provides a powerful means to introduce and express exogenous genes in embryonic stem cells for example for purposes of insertion mutagenesis and for vector expression production of desired proteins.

I claim:

1. An isolated cellular enhancer nucleotide sequence comprising:

CCTGGGCTCTACAGCAGAAGTCTAAGGGGAAAAGCT
TAGGGAGGAATGCCTGGCAAAGGCCCTCATTACTTA
AGAAACAAGTCCTGACTTCAAAGTGAGCTCCCC.

2. A cellular enhancer isolate which permits expression in undifferentiated stem cells of an embryo or teratocarcinoma, of a flanking gene by a promoter operably linked to the gene, which promoter is not normally functional in undifferentiated stem cells of an embryo or teratocarcinoma, said cellular enhancer isolate comprising a nucleotide sequence selected from the group consisting of substantially the following nucleotide essential core sequence in either DNA or RNA form exhibiting the cellular enhancer activity of permitting expression in undifferentiated stem cells of an embryo or teratocarcinoma, of a flanking gene from a promoter operably linked to the gene, which promoter is not normally functional in undifferentiated stem cells of an embryo or teratocarcinoma:

CCTGGGCTCTACAGCAGAAGTCTAAGGGGAAAAGCT
TAGGGAGGAATGCCTGGCAAAGGCCCTCATTACTTA

-continued
AGAAACAAGTCCTGACTTCAAAGTGAGCTCCCC.

3. The cellular enhancer of claim 2 wherein the cellular enhancer comprises the core sequence of approximately 350 bases shown in FIG. 4 as bases 520–870 and which includes the essential core sequence of claim 2 and which includes an enhancer core consensus sequence TTGGAAAG upstream with reference to the direction of transcription of the flanking gene and promoter from said essential core sequence.

4. A recombinant vector selected from the group consisting of plasmids, cosmids, bacteriophages, DNA viruses, RNA viruses and retroviruses, said recombinant vector bearing a nucleotide sequence comprising an inserted gene and operably linked promoter, said gene having desired genetic information necessary for a specified phenotypic trait to be expressed in undifferentiated stem cells of an embryo or teratocarcinoma, said nucleotide sequence further comprising the cellular enhancer of claim 2 flanking said gene and operably linked promoter in effective cellular enhancing relation to said gene and promoter.

5. A recombinant transducing retrovirus carrying a recombinant nucleotide sequence comprising a gene having desired genetic information necessary for a specified phenotypic trait to be expressed in undifferentiated stem cells of an embryo or teratocarcinoma, said gene being operably linked to the retrovirus LTR promoter, said recombinant nucleotide sequence comprising the cellular enhancer of claim 2 flanking said gene and retrovirus LTR promoter in effective cellular enhancing relation to said gene and LTR promoter.

6. A provirus integrated in the genome of an undifferentiated stem cell of an embryo or teratocarcinoma, said provirus carrying a recombinant nucleotide sequence comprising a gene and operably linked promoter, said gene having desired genetic information necessary for a specified phenotypic trait to be expressed in undifferentiated stem cells of the embryo or teratocarcinoma, said recombinant nucleotide sequence comprising the cellular enhancer of claim 2 flanking said gene and operably linked promoter in effective cellular enhancing relation to said gene and promoter.

7. A transformed host animal cell containing a recombinant vector of claim 4, said cell selected from the group consisting of N1H3T3 fibroblasts, embryonic stem (ES) cells, embryonal carcinoma (EC) cells, primordial germ (PG) cells, and mammalian embryo cells.

8. Transformed *Escherichia coli* strain containing a recombinant plasmid vector of claim 4.

9. A transformed undifferentiated stem cell from an embryo or teratocarcinoma, carrying and expressing an inserted gene, a promoter being operably linked to the gene, said operably linked promoter being normally not functional in undifferentiated stem cells of an embryo or teratocarcinoma, said gene and promoter being controlled by the cellular enhancer of claim 2, said cellular enhancer being an insert flanking the gene and operably linked promoter in effective cellular enhancing relation to said gene and promoter.

10. A cell line derived from the stem cell of claim 9.

11. A purified and isolated cellular enhancer sequence which causes transcription and expression in undifferentiated stem cells of an embryo or teratocarcinoma of a flanking gene operably linked to a promoter, which operably linked promoter is not normally functional in undifferentiated stem cells of an embryo or teratocarcinoma, said sequence comprising the core nucleotide shown in FIG. 4 as bases 520–870 and which includes including the sequence set forth in the two lines identified by numbers 651 and 701 of FIG. 4.

12. The cellular enhancer of claim 11 comprising the nucleotide core sequence of approximately 350 bases shown in FIG. 4 bases 520–870 and which includes the sequence set forth in the six lines identified by numbers 551 thru 801 of FIG. 4.

13. A purified and isolated nucleotide sequence with cellular enhancing properties comprising:

```
CTCCAATGGCTGCTTTCCGGAACCCCCAAAGCAGCA
TAAATTGAGTTTAGGATGGACACAGAAATTTGGAAA
GAGGAAGCAACTAATCAACAATGAACTAGAGATGGG
ACCTTGTCCACAGAGCATTGCCTGGGCTCTACAGCA
GAAGTCTAAGGGGAAAAGCTTAGGGAGGAATGCCTG
GCAAAGGCCCTCATTACTTAAGAAACAAGTCCTGAC
TTCAAAGTGAGCTCCCCAGTCCTTAGTATCCCTCAC
CTGAAGTCCTGAGGCTCTGTTTCCCTACTGGGGTCC
ACACTTGTTAACTGCCTAAGCTCAGATCAGCAGCTG
CATATCCTGTTTCTTCCCTGAATTTA.
```

14. A transformed undifferentiated stem cell from an embryo or teratocarcinoma having inserted in the stem cell genome a gene having genetic information necessary for a phenotypic characteristic to be expressed by the cell, a promoter operably linked to said gene, and the nucleotide sequence of claim 13, said nucleotide sequence flanking said gene and operably linked promoter in effective cellular enhancing relation to the gene and promoter, said nucleotide sequence permitting the undifferentiated stem cell to express said selected phenotypic trait.

15. A cell line derived from the stem cell of claim 14.

16. A plasmid vector contruct comprising the cellular enhancer of claim 13.

17. *Escherichia coli* strain containing a plasmid of claim 16.

18. A recombinant nucleotide sequence comprising:
a gene having desired genetic information necessary for a specified phenotypic trait to be expressed in undifferentiated stem cells of an embryo or teratocarcinoma;
a promoter operably linked to the gene;
and a cellular enhancer flanking the gene and operably linked promoter in effective cellular enhancing relation to the gene and promoter, said cellular enhancer being characterized by the cellular enhancing activity of permitting expression of the gene from the promoter when the recombinant nucleotide sequence is introduced into an undifferentiated stem cell of an embryo or teratocarbinoma, said gene and operably linked promoter being not normally functional in undifferentiated stem cells;
said cellular enhancer comprising a nucleotide sequence selected from the group consisting of the following nucleotide essential core sequence exhibiting the cellular enhancer activity of permitting expression in undifferentiated stem cells from an embryo of a flanking gene by a promoter operably linked to the gene, which promoter is not normally functional in undifferentiated stem cells of an embryo or teratocarcinoma:

```
CCTGGGCTCTACAGCAGAAGTCTAAGGGGAAAAGCT
TAGGGAGGAATGCCTGGCAAAGGCCCTCATTACTTA
AGAAACAAGTCCTGACTTCAAAGTGAGCTCCCC.
```

19. A vector containing the recombinant nucleotide sequence of claim 18.

20. A cellular host transformed by the vector of claim 19.

21. An undifferentiated stem cell host from an embryo or teratocarcinoma transformed by the vector of claim 19.

22. A method for expressing a gene not normally expressed in undifferentiated stem cells comprising culturing the transformed host cell of claim 21.

* * * * *